United States Patent [19]

Stephan

[11] 4,024,284
[45] May 17, 1977

[54] ETHYL- AND VINYLBENZENES AS ANTI-INFLAMMATORY AGENTS

[75] Inventor: Erwin A. Stephan, Indianapolis, Ind.

[73] Assignee: Eli Lilly and Company, Indianapolis, Ind.

[22] Filed: May 26, 1976

[21] Appl. No.: 690,217

Related U.S. Application Data

[62] Division of Ser. No. 584,999, June 9, 1975, Pat. No. 3,975,543.

[52] U.S. Cl. .............................. 424/340; 424/353; 424/356
[51] Int. Cl.² ............... A61K 31/03; A61K 31/015; A61K 31/085
[58] Field of Search ................... 424/340, 353, 356

*Primary Examiner*—Stanley J. Friedman
*Attorney, Agent, or Firm*—William E. Maycock; Everet F. Smith

[57] ABSTRACT

A method of treating inflammation in warm-blooded animals, employing an ethyl- or vinylbenzene as the active anti-inflammatory agent.

24 Claims, No Drawings

ETHYL- AND VINYLBENZENES AS ANTI-INFLAMMATORY AGENTS

This is a division of application Ser. No. 584,999 filed June 9, 1975, now U.S. Pat. No. 3,975,543.

BACKGROUND OF THE INVENTION

This invention relates to a method of treating inflammation in warm-blooded animals, employing an ethyl- or vinylbenzene as the active anti-inflammatory agent.

Warm-blooded animals, including humans, are known to suffer from various conditions involving inflammation with concomitant swelling, tenderness, decreased mobility, pain, and fever. While a number of anti-inflammatory agents are effective in the symptomatic treatment of such inflammatory conditions as rheumatoid arthritis, rheumatoid spondylitis, osteo-arthritis, degenerative joint diseases, and the like, many such agents have a number of undesirable side effects, such as gastric irritation and the like. Certain ethyl- and vinylbenzenes, defined hereinafter, now have been discovered to be active anti-inflammatory agents, even though many of such compounds are known.

SUMMARY OF THE INVENTION

In accordance with the present invention, a method of treating inflammation in warm-blooded animals is provided which comprises administering to a warm-blooded animal in need of such treatment an amount effective for treating inflammation of an ethyl- or vinylbenzene having the following general formula:

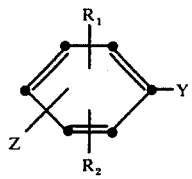

wherein Y is a monovalent group which is either ethyl or vinyl; $R_1$ and $R_2$ are monovalent groups independently selected from the group consisting of hydrogen, halo, $C_1$–$C_3$ alkyl, and $C_1$–$C_3$ alkoxy; and Z is a monovalent group which is either $C_5$–$C_7$ cycloalkyl, with the proviso that at least one of $R_1$ and $R_2$ must be other than hydrogen, or a group of the formula,

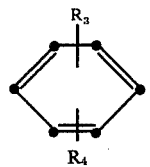

wherein $R_3$ and $R_4$ are monovalent groups independently selected from the group consisting of hydrogen, halo, $C_1$–$C_3$ alkyl, and $C_1$–$C_3$ alkoxy, with the proviso that at least one of $R_1$, $R_2$, $R_3$, and $R_4$ must be other than hydrogen.

DETAILED DESCRIPTION OF THE INVENTION

As used herein, the term "halo" is meant to include fluoro, chloro, bromo, and iodo.

According to the method of the present invention, inflammation in a warm-blooded animal is treated by administering to a warm-blooded animal in need of such treatment an amount effective for treating inflammation of an ethyl- or vinylbenzene as defined hereinbefore, thereby alleviating symptoms of inflammation. While the circumstances causing such symptoms are many, the compounds to be employed in the method of the present invention are especially suited in the management of rheumatoid arthritis. However, those skilled in the art will recognize that the present method also will be effective in the treatment of numerous other conditions which produce inflammation, such as rheumatoid spondylitis, degenerative joint disease, and minor conditions of inflammation of unspecified origin.

To utilize such ethyl- or vinylbenzene in the method of the present invention, such compound is administered to a warm-blooded animal parenterally, enterally, or in the form of rectal suppositories, with oral administration being preferred. Such compound is administered in an effective amount, typically from about 0.05 to about 1000 mg./kg. of animal body weight. Such administration can consist of a single dose or up to about six smaller doses per day.

The compound preferably is employed in combination with one or more adjuvants suited to the particular route of administration. Thus, in the case of oral administration, the compound is modified with pharmaceutical diluents or carriers, such as lactose, sucrose, starch powder, cellulose, talc, magnesium stearate, magnesium oxide, calcium sulfate, acacia powder, gelatin, sodium alginate, sodium benzoate, and stearic acid. The resulting composition can be formulated in tablets or enclosed in capsules for convenient administration. The compound also can be mixed with an appropriate liquid and administered as an elixir, suspension, or the like. In the case of parenteral administration, the compound to be used is conveniently formulated in saline to constitute an injectable liquid solution or suspension. Other adjuvants and modes of administration are known to those skilled in the art. If desired, the pharmaceutical composition can contain, in addition to a compound of the present invention, one or more other pharmacologically-active substances, such as acetylsalicylic acid, α-d-propoxyphene, caffeine, and acetaminophen (N-acetyl-p-aminophenol).

The anti-inflammatory activities of the ethyl- and vinylbenzenes which are employed in the method of the present invention are readily demonstrated by either the erythema blocking test of C. V. Winder, et al., Arch. Int. Pharmacodyn., 116, 261 (1958), or the anti-inflammatory edema test of C. A. Winter, et al., Proc. Soc, Exp. Biol. Med., 111, 544 (1962).

Examples of ethyl- and vinylbenzenes suitable for use in the method of the present invention include, among others:

3-chloro-4-cyclohexyl-1-ethylbenzene,
1-ethyl-4-(2-fluorophenyl)benzene,
1-ethyl-3-(3-fluorophenyl)benzene,
4-(2-chlorophenyl)-1-ethylbenzene,
1-ethyl-4-(2,4-difluorophenyl)benzene,
1-ethyl-2-(3,5-difluorophenyl)benzene,
1-ethyl-4-(2,5-difluorophenyl)benzene,
1-ethyl-4-(2,6-difluorophenyl)benzene,
1-ethyl-4-(2-methylphenyl)benzene,
1-ethyl-2-(3-methylphenyl)benzene,
1-ethyl-4-(2-methoxyphenyl)benzene,
1-ethyl-3-fluoro-4-phenylbenzene,
1-ethyl-4-fluoro-3-phenylbenzene,
2-chloro-1-ethyl-4-phenylbenzene,
1-ethyl-3-methoxy-4-phenylbenzene,
1-ethyl-5-methoxy-2-phenylbenzene, 1-ethyl-3-fluoro-4-(2-fluorophenyl)benzene,
1-ethyl-3-(2-fluorophenyl)-5-methoxybenzene,
4-cyclohexyl-3-fluoro-1-vinylbenzene,
4-(2-fluorophenyl)-1-vinylbenzene,
3-(2,5-difluorophenyl)-1-vinylbenzene,
4-(3,5-difluorophenyl)-1-vinylbenzene,
2-(2,6-difluorophenyl)-1-vinylbenzene,
4-(2,6-difluorophenyl)-1-vinylbenzene,
4-(2-methylphenyl)-1-vinylbenzene,
3-(2-methoxyphenyl)-1-vinylbenzene,
2-fluoro-4-phenyl-1-vinylbenzene,
4-chloro-3-phenyl-1-vinylbenzene,
3-methoxy-4-phenyl-1-vinylbenzene, and
3-fluoro-4-(2-fluorophenyl)-1-vinylbenzene.

The preferred ethyl- and vinylbenzenes are those compounds wherein Z in the general formula defined hereinbefore is the group,

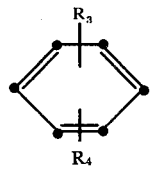

Examples of such preferred compounds include, among others:
1-ethyl-4-(2-fluorophenyl)benzene,
4-(2-chlorophenyl)-1-ethylbenzene,
1-ethyl-3-methoxy-4-phenylbenzene,
1-ethyl-4-(3-fluorophenyl)benzene,
1-ethyl-4-(2-methylphenyl)benzene,
1-ethyl-4-(2,4-difluorophenyl)benzene,
1-ethyl-4-(2,5-difluorophenyl)benzene,
1-ethyl-4-(2,6-difluorophenyl)benzene,
1-ethyl-3-fluoro-4-(2-fluorophenyl)benzene,
4-(2-fluorophenyl)-1-vinylbenzene,
4-(2-chlorophenyl)-1-vinylbenzene,
3-methoxy-4-phenyl-1-vinylbenzene,
4-(3-fluorophenyl)-1-vinylbenzene,
4-(2-methylphenyl)-1-vinylbenzene,
4-(2,4-difluorophenyl)-1-vinylbenzene,
4-(2,5-difluorophenyl)-1-vinylbenzene,
4-(2,6-difluorophenyl)-1-vinylbenzene, and
3-fluoro-4-(2-fluorophenyl)-1-vinylbenzene.

A most preferred group of ethyl- and vinylbenzenes are those compounds wherein Z is the group,

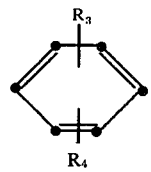

and $R_1$, $R_2$, $R_3$, and $R_4$ independently are hydrogen or halo with at least one of $R_1$, $R_2$, $R_3$, and $R_4$ being halo. The preferred halo groups are fluoro and chloro. Examples of such compounds have been listed hereinabove.

The ethyl- and vinylbenzenes which can be employed in the method of the present invention are prepared by known methods from the corresponding acetophenones; ethyl-, vinyl-, and ethylnylbenzenes; benzaldehydes; phenyl methyl carbinols; and the like. Such intermediates are readily prepared by known methods, usually from the appropriate cycloalkyl- and phenylbenzenes. The cycloalkyl- and phenylbenzenes in turn are readily prepared by known methods.

It will be apparent to one skilled in the art that all of the ethyl- and vinylbenzenes suitable for use in the method of the present invention cannot be prepared by any one procedure or reaction scheme. However, the limitations inherent in any given procedure are well understood by one skilled in the art, and such limitations can be avoided either by appropriate molecular manipulations or by the use of alternative synthetic procedures.

The present invention is further described, but not limited, by the following examples which illustrate preferred procedures for the preparation of the ethyl- and vinylbenzenes to be employed in the method of the present invention. All temperatures are in degrees centigrade.

EXAMPLE 1

Preparation of 1-ethyl-4-(2-fluorophenyl)benzene

1-Ethynyl-4-(2-fluorophenyl)benzene, 22 g., was reduced in a Parr Instrument Company Series 3910 Low-Pressure Shaker-Type Apparatus, using 100 ml. of benzene, 2 g. of five percent palladium on charcoal, and 0.5 ml. of concentrated sulfuric acid. Reduction was carried out at room temperature and at an initial hydrogen pressure of 50 psig. Within 15 minutes, the hydrogen pressure had dropped to 32 psig. Hydrogen pressure was increased to 52 psig. and agitation continued for 2 hours, with no additional hydrogen pressure drop. The reaction mixture was filtered and the filtrate was neutralized with 2 percent aqueous sodium carbonate. The resulting mixture was washed with water. The benzene phase was separated, dried over anhydrous sodium sulfate, and filtered. The benzene was evaporated and the residue was vacuum distilled to give 17 g. of 1-ethyl-4-(2-fluorophenyl)benzene, bp 99°–101° / 0.3 mm. The following elemental analysis was obtained:

Calculated for $C_{14}H_{13}F$: C, 83.97; H, 6.54; F, 9.49. Found: C, 84.23; H, 6.39; F, 9.42.

EXAMPLE 2

Preparation of 1-ethyl-4-(4-fluorophenyl)benzene

The procedure of Example 1 was repeated, except that the 1-ethynyl-4-(2-fluorophenyl)benzene was replaced with 1.5 g. of 1-ethynyl-4-(4-fluorophenyl)benzene, the amount of catalyst was reduced to 0.5 g., the sulfuric acid was omitted, initial hydrogen pressure was 48 psig., and the reduction was allowed to proceed overnight. Evaporation of the benzene left a solid which was recrystallized from hexane to give 1-ethyl-4-(4-fluorophenyl)benzene, mp 60°–63°. The following elemental analysis was obtained:

Calculated for $C_{14}H_{13}F$: C, 83.97; H, 6.54; F, 9.49. Found: C, 84.02; H, 6.35; F, 9.37.

EXAMPLE 3

Preparation of 1-ethyl-4-(2-chlorophenyl)benzene

The procedure of Example 1 was repeated, except that the 1-ethynyl-4-(2-fluorophenyl)benzene was replaced with 23.1 g. of 4'-(2-chlorophenyl)acetophenone, the amount of benzene was increased to 150 ml., the amount of catalyst was increased to 3 g., the amount of sulfuric acid was increased to 2 ml., and the reduction was allowed to proceed for 13 hours. Evaporation of the benzene left a residue which was vacuum distilled to give 14 g. of 1-ethyl-4-(2-chlorophenyl)benzene, bp 110°-112°/0.4 mm. The following elemental analysis was obtained:

Calculated for $C_{14}H_{13}Cl$: C, 77.49; H, 6.05; Cl, 16.36. Found: C, 77.79; H, 5.79; Cl, 16.18.

EXAMPLE 4 preparation of 1-ethyl-4-(4-chlorophenyl)benzene

The procedure of Example 3 was repeated, except that the 4'-(2-chlorophenyl)acetophenone was replaced with an equal amount of 4'-(4-chlorophenyl)acetophenone, the amount of benzene employed was increased to 200 ml., and the amount of sulfuric acid was reduced to 5 drops. After 7 hours, hydrogen pressure had dropped to 35.5 psig. Evaporation of the benzene left a solid which, according to nuclear magnetic resonance analysis, contained only about 67 percent of the desired ethylbenzene. Consequently, the solid was subjected to the hydrogenation procedure again, using 200 ml. of benzene, 2 g. of catalyst, and 1 ml. of concentrated sulfuric acid. The solid obtained upon evaporation of the benzene was recrystallized from hexane, giving 1-ethyl-4-(4-chlorophenyl)benzene, mp 103°-104°. The following elemental analysis was obtained:

Calculated for $C_{14}H_{13}Cl$: C, 77.59; H, 6.05; Cl, 16.36. Found: C, 77.80; H, 5.98; Cl, 16.17.

EXAMPLE 5

Preparation of 4-(2-fluorophenyl)-1-vinylbenzene

1-Ethynyl-4-(2-fluorophenyl)benzene, 29.6 g., was reduced in a Parr Instrument Company Series 3910 Low-Pressure Shaker-Type Apparatus, using 450 ml. of pyridine, and 0.3 g. of 5 percent palladium on barium sulfate; reduction was carried out at room temperature for 30 minutes and at an initial hydrogen pressure of 30 psig. The reaction mixture was filtered and the filtrate was evaporated in vacuo. The residue was vacuum distilled to give 20.5 g. of solid which was recrystallized from methanol to give 4-(2-fluorophenyl)-1-vinylbenzene, mp 38°. The material contained traces of pyridine and 1-ethyl-4-(2-fluorophenyl)benzene, as shown by nuclear magnetic resonance analysis. The following elemental analysis was obtained:

Calculated for $C_{14}H_{11}F$: C, 84.82; H, 5.59; F, 9.58. Found: C, 84.49; H, 4.54; F, 9.23.

What is claimed is:
1. A method of treating inflammation in warm-blooded animals which comprises administering to a warm-blooded animal in need of such treatment an amount effective for treating inflammation of a compound of the formula,

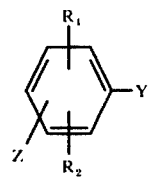

wherein Y is a monovalent group which is either ethyl or vinyl; $R_1$ and $R_2$ are monovalent groups independently selected from the group consisting of hydrogen, halo, $C_1$-$C_3$ alkyl, and $C_1$-$C_3$ alkoxy, and Z is a monovalent group which is either $C_5$-$C_7$ cycloalkyl, with the provisos that at least one of $R_1$ and $R_2$ must be other than hydrogen and when Y is ethyl, $R_1$ and $R_2$ must be other than halo, or a group of the formula,

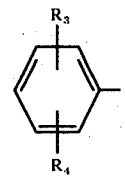

wherein $R_3$ and $R_4$ are monovalent groups independently selected from the group consisting of hydrogen, halo, $C_1$-$C_3$ alkyl, and $C_1$-$C_3$ alkoxy, with the provisos that at least one of $R_1$, $R_2$, $R_3$, and $R_4$ must be other than hydrogen and when Y is ethyl, $R_1$, $R_2$, $R_3$, and $R_4$ must be other than halo.

2. The method of claim 1, wherein such compound is administered at a level of from about 0.05 to about 1000 mg./kg. of animal body weight.

3. The method of claim 1, wherein Z is $C_5$-$C_7$ cycloalkyl and $R_1$ and $R_2$ independently are selected from the group consisting of hydrogen, fluoro, chloro, methyl, and methoxy.

4. The method of claim 1, wherein Z is the group of the formula,

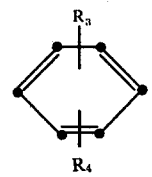

5. The method of claim 4, wherein $R_1$, $R_2$, $R_3$, and $R_4$ independently are selected from the group consisting of hydrogen, methyl, and methoxy.

6. The method of claim 5, wherein Y is ethyl.

7. The method of claim 6, wherein three of $R_1$, $R_2$, $R_3$, and $R_4$ are hydrogen.

8. The method of claim 7, wherein the compound is 1-ethyl-3-methoxy-4-phenylbenzene.

9. The method of claim 7, wherein the compound is 1-ethyl-4-(2-methylphenyl)benzene.

10. The method of claim 5, wherein Y is vinyl.

11. The method of claim 10, wherein three of $R_1$, $R_2$, $R_3$, and $R_4$ are hydrogen.

12. The method of claim 11, wherein the compound is 3-methoxy-4-phenyl-1-vinylbenzene.

13. The method of claim 11, wherein the compound is 4-(2-methylphenyl)-1-vinylbenzene.

14. The method of claim 1, wherein Y is vinyl Z is the group of the formula,

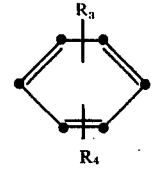

and $R_1$, $R_2$, $R_3$, and $R_4$ independently are hydrogen or halo with at least one of $R_1$, $R_2$, $R_3$, and $R_4$ being halo.

15. The method of claim 14, wherein $R_1$, $R_2$, $R_3$, and $R_4$ independently are selected from the group consisting of hydrogen, fluoro, and chloro.

16. The method of claim 15, wherein three of $R_1$, $R_2$, $R_3$, and $R_4$ are hydrogen.

17. The method of claim 16, wherein the compound is 4-(2-fluorophenyl)-1-vinylbenzene.

18. The method of claim 16, wherein the compound is 4-(2-chlorophenyl)-1-vinylbenzene.

19. The method of claim 16, wherein the compound is 4-(3-fluorophenyl)-1-vinylbenzene.

20. The method of claim 15, wherein two of $R_1$, $R_2$, $R_3$, and $R_4$ are hydrogen.

21. The method of claim 20, wherein the compound is 4-(2,4-difluorophenyl)-1-vinylbenzene.

22. The method of claim 20, wherein the compound is 4-(2,5-difluorophenyl)-1-vinylbenzene.

23. The method of claim 20, wherein the compound is 4-(2,6-difluorophenyl)-1-vinylbenzene.

24. The method of claim 20, wherein the compound is 3-fluoro-4-(2-fluorophenyl)-1-vinylbenzene.

* * * * *

UNITED STATES PATENT AND TRADEMARK OFFICE
CERTIFICATE OF CORRECTION

PATENT NO. : 4,024,284
DATED : May 17, 1977
INVENTOR(S) : Erwin A. Stephan

It is certified that error appears in the above-identified patent and that said Letters Patent are hereby corrected as shown below:

On the Title Page, under "Related U.S. Application Data", following the term "3,975,543", please insert --which is a continuation-in-part of Serial No. 485,875, July 5, 1974, abandoned--.

Signed and Sealed this

Eighth Day of April 1980

[SEAL]

Attest:

SIDNEY A. DIAMOND

Attesting Officer

Commissioner of Patents and Trademarks